United States Patent [19]

Kashket

[11] Patent Number: 5,210,032
[45] Date of Patent: May 11, 1993

US005210032A

[54] DEGENERATION-RESISTANT SOLVENTOGENIC CLOSTRIDIA

[75] Inventor: Eva R. Kashket, Newton, Mass.

[73] Assignee: Trustees of the Boston University, Boston, Mass.

[21] Appl. No.: 822,802

[22] Filed: Jan. 21, 1992

[51] Int. Cl.$^5$ .......................... C12P 7/28; C12P 7/36; C12P 7/16; C12R 1/142
[52] U.S. Cl. .................................. 435/150; 435/151; 435/152; 435/153; 435/154; 435/160; 435/842
[58] Field of Search .............. 435/150, 151, 152, 153, 435/154, 160, 842

[56] References Cited

U.S. PATENT DOCUMENTS

| | | | |
|---|---|---|---|
| 4,521,516 | 6/1985 | Lemme et al. | 435/150 |
| 4,539,293 | 9/1985 | Bergstrom | 435/160 |
| 4,560,658 | 12/1985 | Datta et al. | 435/160 |
| 4,757,010 | 7/1988 | Hermann et al. | 435/150 |
| 5,063,156 | 11/1991 | Glassner et al. | 435/150 |

*Primary Examiner*—Herbert J. Lilling
*Attorney, Agent, or Firm*—Paul J. Cook

[57] ABSTRACT

Butanol and acetone are major end products of a bacterial fermentation process carried out by anaerobic saccharolytic clostridia such as *Clostridium acetobutylicum*. However, these organisms degenerate upon repeated subculture of growing cells, thereby losing their capacity to produce solvents and to develop into spores. A novel class of degeneration-resistant mutants of *C. acetobutylicum*, generated by transposon insertion mutagenesis, has been produced employing a novel selection procedure. Upon subculture the mutant cells survive significantly longer than the parental cells without altered solventogenic characteristics. The mutant organism, the technique for its isolation and its use are provided.

1 Claim, No Drawings

DEGENERATION-RESISTANT SOLVENTOGENIC CLOSTRIDIA

BACKGROUND OF THE INVENTION

This invention relates to the production of new bacterial strains of butanol and acetone-producing bacteria with improved growth characteristics.

At the present time, butanol and acetone can be produced by biological processes by incubating feedstock material, including molasses, corn steep liquor or other carbohydrates, with a variety of strains of *Clostridium acetobutylicum* and related saccharolytic clostridia. However, the wild type strains of *C. acetobutylicum* characteristically degenerate, that is, lose the capacity to produce solvents and to sporulate. This phenomenon occurs upon repeated subculture of growing clostridial cells. Degenerate cells cannot switch from producing acids to producing solvents and spores, and therefore, die. Degeneration thus limits the length of time one can use the cells without restarting the cultures by germinating spores. Different wild type strains of *C. acetobutylicum* degenerate at different rates.

Accordingly, it would be desirable to obtain degneration-resistant mutants capable of producing butanol and acetone from commonly available feedstocks. Such microorganisms would be capable of producing these desired chemicals over extended time periods while reducing the frequency of restarting the culture. Such strains also are useful for development of fermentation by continuous cultures or immobilized solventogenic clostridia. Furthermore, it would be desirable to have a means for producing these mutant microorganisms, employing procedures for identifying and selecting microorganisms with the desired longevity characteristics.

SUMMARY OF THE INVENTION

In accordance with this invention, a new bacterial strain is provided. It is a mutant of the *Clostridium acetobutylicum*, which unlike the parental strain, is resistant to degeneration, but is unaffected in the production of butanol and acetone. This mutant can be generated by one of the available mutagenesis techniques, the insertion of a transposon into the bacterial chromosomes. The mutant strain is identified and isolated by a novel technique developed to quantify the rate of clostridial degeneration. This mutant and others produced by the same methods can be utilized either alone to ferment sugars to alcohols and solvents, in combination with other bacteria that convert insoluble carbohydrates, such as cellulose to simple sugars or with chemically pretreated insoluble carbohydrates.

DESCRIPTION OF SPECIFIC EMBODIMENTS

The bacterial strain utilized in the present invention is produced by mutation of *Clostridium acetobutylicum* with a mutagenic agent resulting in a mutant strain resistant to degeneration. The novel microorganisms of this invention are strains of *Clostridium acetobutylicum* which exhibit the following characteristics:

The parental (wild type) strain used, *Clostridium acetobutylicum* NCIB 8052, degenerates readily upon subculture, and, under the conditions of the experimentation, no viable cells are left after 50-80 generations of growth. In contrast, the degeneration-resistant mutant of this invention survive for 150-240 generations or more.

A mutant strain utilized in the present invention has been assigned ATTC No. 55-245 by the American Type Culture Collection, 12301 Parklawn Drive, Rockville, Md. 20852. All restrictions on availability to the public of this mutant strain so-deposited will be irrevocably removed upon granting of a patent based upon this application.

Transposon-insertion mutagenisis is employed to generate mutants of *C. acetobutylicum*. Other methods, including chemical mutagenesis, can also be employed. Transposable elements (transposons) are specific, discrete DNA segments that can spread by being copied at new sites in bacterial chromosomes, plasmids or virus genomes. Useful transposons contain antibiotic resistance genes (e.g., for erythromycin), which permit selection of transposon-containing cells. Transposons insert themselves into a variety of genes, often disrupting their function and causing mutations. To select and identify a specific mutant, antiobiotic-resistant cells are subjected to selective pressures for the desired characteristics, whenever that is possible, and then assayed for specific mutated genes.

However, no selective processes for degeneration resistance in clostridia is presently available. Moreover, to identify degeneration resistant mutants the methods used must balance a number of factors that affect cell growth and viability. These factors include acid production by degenerate cells, which causes death of all the cells in the culture, the rates of growth, rates of sporulation of the nondegenerate cells, and others. Therefore, a novel protocol for subculturing the cells is utilized herein to quantitate degeneration rates, and thus identify cells that degnerate less rapidly than the parental cells.

By the phrase "resistant to degeneration" as applied to a mutant strain of *Clostridium acetobutylicum* of this invention is meant a mutant strain capable of reproducing for at least 150 generations when subcultured under conditions in which its parent, strain NCIB 8052, survives 50-80 generations.

In use, wild strains of *Clostridium acetobutylicum* have been used in batch culture for the industrial production of solvents from sugars. Fermentations in continuous culture or by immobilized cells has not yet been developed for practical use. The mutant strain of this invention is utilized to effect the same fermentations as the wild type, using a variety of sugars, such as glucose, fructose or mixtures thereof, as well as molasses, whey, and pretreated agricultural waste materials, such as wood shavings, rice straw, mycotoxin-contaminated grains, etc. However, the degeneration resistant mutant of this invention is advantageous because it suffers less than the wild type from limitations due to cell degeneration, rendering it useful for batch and continuous processes. In addition, new mutants derived by the novel protocol with greater degeneration resistance afford further advantage for efficient fermentation.

The following examples illustrate the present invention and are not intended to limit the same:

EXAMPLE I

This example illustrates the formation and selection of a mutant strain of a *Clostridium acetobutylicum* useful in the process of this invention. Using a published method (Wooley et al., J. Appl. Bacteriol. 69, 718-728, 1989) *Clostridium acetobutylicum* NCIB 8052 cells, available from the National Cellection of Industrial Bacteria, Aberdeen, Scotland, were mated with the donor cells, *Enterococcus faecalis* BM 4110 that contain transposon Tn1545 in their chromosomes. After mating, erythromycin-resistant clostridial cells containing Tn1545 were selected by growth on media selective for clostridia and containing antibiotics. Pure strains were isolated and tested individually for degeneration utilizing the novel technique developed for identifying and quantitating degeneration. The protocol consisted of subculturing the cells every 2 days by inoculating 1 ul of culture in 1 ml of rich growth medium containing 6% glucose and antibiotics, and incubating them at 35° C.; growth starting from a 1 to 1000 dilution of the innoculum is approximately equivalent to 10 generations. All manipulations were carried out within an anaerobic glove box. The process was repeated every 2 days until no growth (turbidity of the cultures) was seen. Samples of the cultures were plated onto agar plates since colonies formed by degenerate and nondegenerate cells are easily distinguished by the naked eye. The number of viable cells was determined from the number of colonies. The cellular morphology was followed by phase contrast light microscopy, since nondegenerate cells differentiate into spores and degenerate cells do not. The ability of the cultures to produce solvents (butanol and acetone) was detected by the change in culture acidity (pH) and measured by gas chromatography. The percentage of degenerate cells in the culture increased during the last 2-3 subcultures, until growth was no longer seen. The number of generations attained before the subcultures were totally degenerate and the cells had died, probably due to excess acidification, and no viable spores were present is taken as the end point for degeneration resistance.

In 4 separate mating experiments, approximately 200 individual mutants were examined. The degeneration-resistant mutant cells survive beyond 150-240 generations as compared to the wild type *C. acetobutylicum* which survived only 50-80 generations under the conditions employed. The approximately 3-fold difference in longevity between the parent cells and the mutant cells is significant.

What is claimed is:

1. A process for producing butanol and acetone comprising the step of:

growing a mutant strain of *Clostridium acetobutylicum* ATTC 55245 which is resistant to degeneration in a growth medium containing at least one sugar and recovering butanol and acetone from said growth medium wherein said mutant strain reproduces for at least 150 generations.

* * * * *

UNITED STATES PATENT AND TRADEMARK OFFICE
CERTIFICATE OF CORRECTION

PATENT NO. : 5,210,032
DATED : May 11, 1993
INVENTOR(S) : Eva Kasket

It is certified that error appears in the above-indentified patent and that said Letters Patent is hereby corrected as shown below:

Column 1, line 4, insert the following information:
 -This invention was made with Government support under grant number 88-37233-40636 awarded by the U.S. Department of Agriculture. The Government has certain rights to this invention.-

Signed and Sealed this

Second Day of January, 1996

Attest:

BRUCE LEHMAN

*Attesting Officer*     *Commissioner of Patents and Trademarks*